US011155830B2

(12) United States Patent
Li et al.

(10) Patent No.: US 11,155,830 B2
(45) Date of Patent: Oct. 26, 2021

(54) PREPARATION AND USE OF NANOPARTICLE-DOPED RNA HYDROGEL TARGETING TO TRIPLE NEGATIVE BREAST CANCER

(71) Applicant: LINYI UNIVERSITY, Linyi (CN)

(72) Inventors: Xuemei Li, Linyi (CN); Xiaofan Liu, Linyi (CN); Lairong Ding, Linyi (CN); Shusheng Zhang, Linyi (CN)

(73) Assignee: LINYI UNIVERSITY, Linyi (CN)

( * ) Notice: Subject to any disclaimer, the term of this patent is extended or adjusted under 35 U.S.C. 154(b) by 0 days.

(21) Appl. No.: 16/825,707

(22) Filed: Mar. 20, 2020

(65) Prior Publication Data
US 2021/0017537 A1    Jan. 21, 2021

(30) Foreign Application Priority Data
Jul. 18, 2019  (CN) .......................... 201910648136.6

(51) Int. Cl.
| | | |
|---|---|---|
| *A61K 48/00* | (2006.01) | |
| *C07H 21/04* | (2006.01) | |
| *C12N 15/85* | (2006.01) | |
| *A61K 47/54* | (2017.01) | |
| *A61P 35/00* | (2006.01) | |
| *A61K 9/06* | (2006.01) | |
| *C12N 15/113* | (2010.01) | |
| *C12N 15/115* | (2010.01) | |

(52) U.S. Cl.
CPC ............... *C12N 15/85* (2013.01); *A61K 9/06* (2013.01); *A61K 47/549* (2017.08); *A61K 47/554* (2017.08); *A61P 35/00* (2018.01); *C12N 15/113* (2013.01); *C12N 15/115* (2013.01); *C12N 2310/11* (2013.01); *C12N 2310/141* (2013.01); *C12N 2310/16* (2013.01); *C12N 2310/3515* (2013.01); *C12N 2320/32* (2013.01); *C12N 2330/30* (2013.01); *C12N 2800/00* (2013.01)

(58) Field of Classification Search
CPC ....................... C12N 15/113; C12N 2310/141
See application file for complete search history.

(56) References Cited

FOREIGN PATENT DOCUMENTS

WO    WO 2017/044768 A1 *  3/2017  ........... C12N 15/113

OTHER PUBLICATIONS

Sanchez-Sendra et al. (Scientific Reports, 2018, 8, 17076, 1-14).*
Han et al. (Biomaterials, 185, 2018, 205-218).*
Zhu et al. (Advanced Functional Materials, 26, 30, 2016, 5490-5498).*
Sun et al. (Ther. Deliv., 2015, 6(7), 765-768).*

* cited by examiner

Primary Examiner — Amy H Bowman
(74) Attorney, Agent, or Firm — Hauptman Ham, LLP

(57) ABSTRACT

The present invention discloses preparation and use of a nanoparticle-doped RNA hydrogel targeting to a triple negative breast cancer (TNBC). The RNA hydrogel is a pure RNA system formed in a rolling circle transcription manner. The transcription process generates a large number of GC bonds, which provides a large number of sites for the introduction of DOX. The large number of RNA copy structures generated by rolling circle replication is a polyanionic aggregate. Due to the strong electronegativity of the polyanionic aggregate, electropositive $MnO_2$@Ce6 nanoparticles are introduced, such that the colloid cationic $MnO_2$@Ce6 particles can be stabilized by the polyanionic hydrogel, and thus target into a breast cancer cell for synergistic treatment. It can be used for a drug slow release system, has good biocompatibility, and has broad prospects in the fields of growth inhibition effects on targeted MDA-MB-231 tumor cells, inhibition of cancer metastasis and recurrence, and the like.

9 Claims, 10 Drawing Sheets
Specification includes a Sequence Listing.

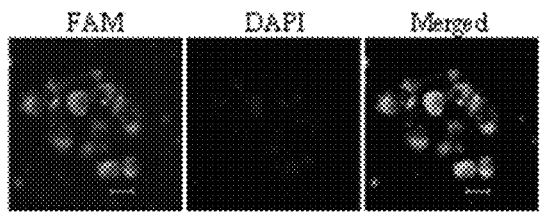
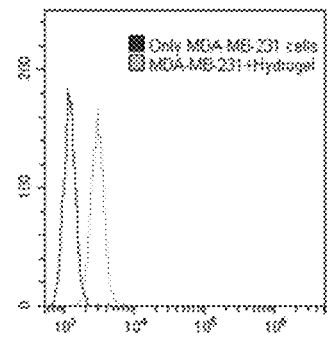
FIG. 7A
FIG. 7B
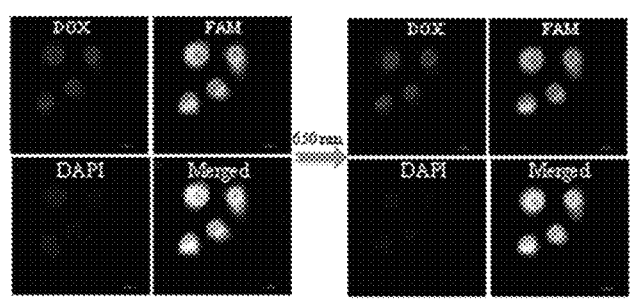
FIG. 7C
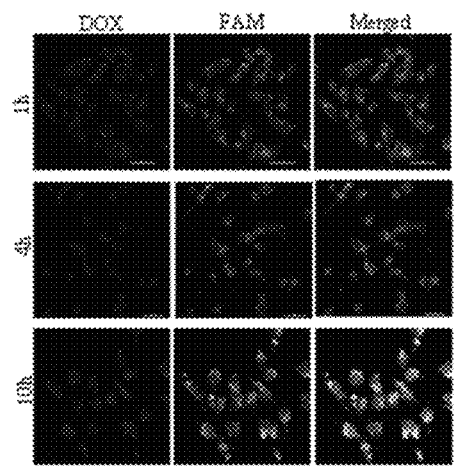
FIG. 7D

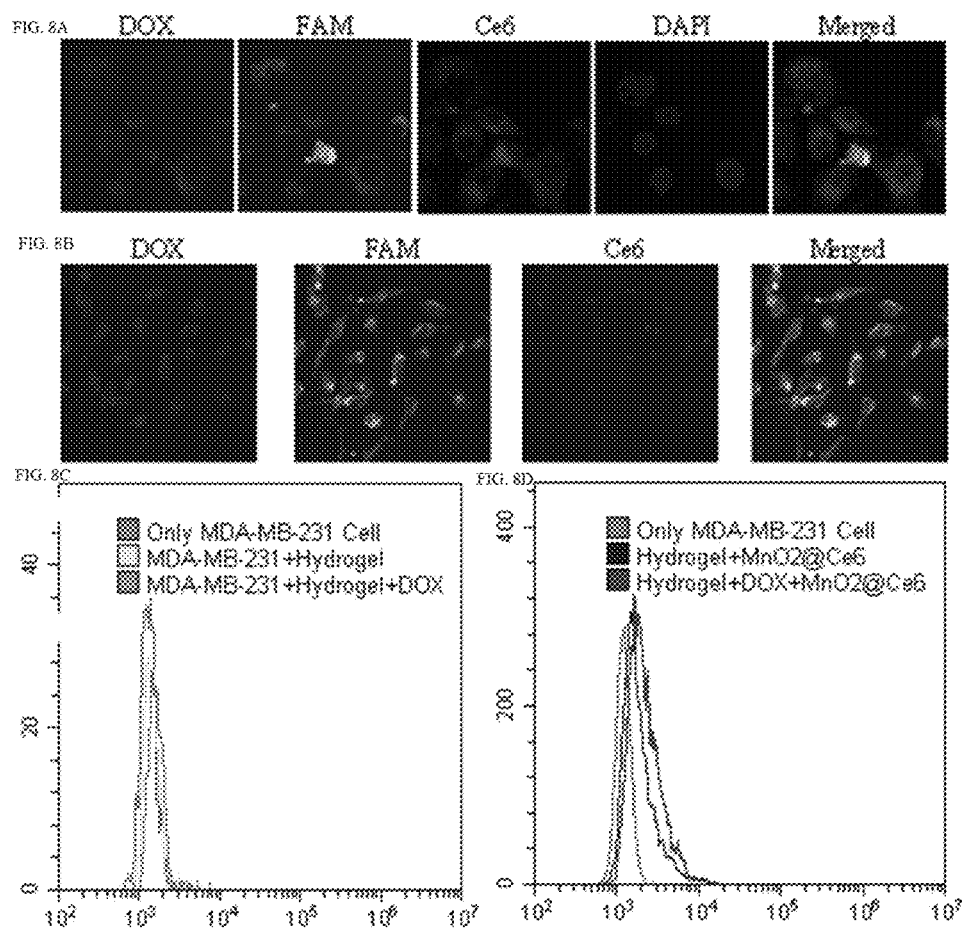

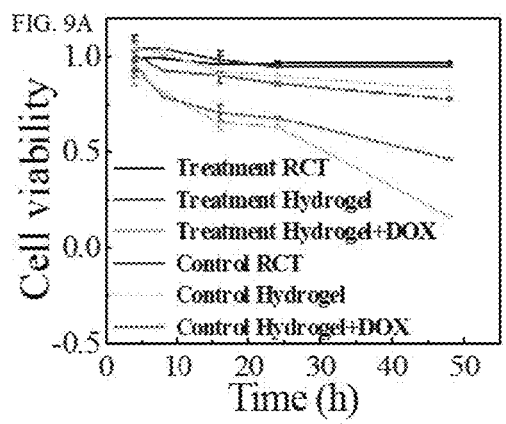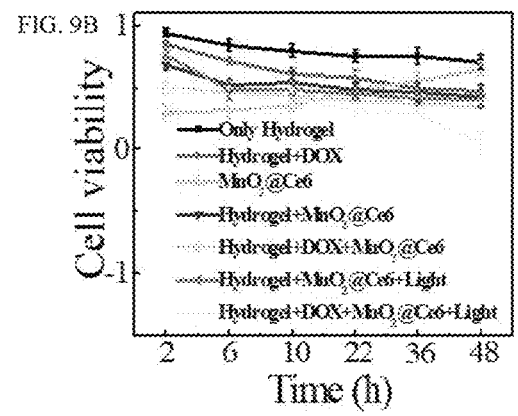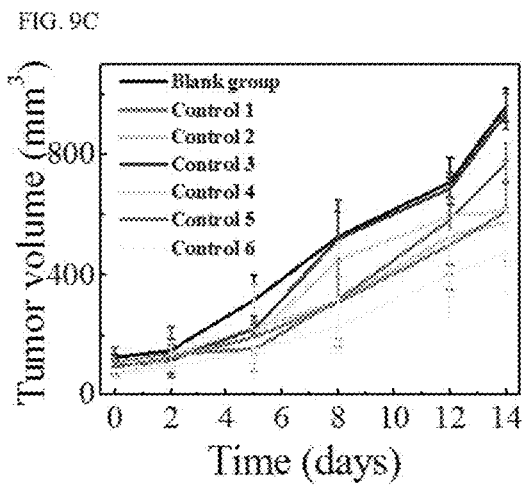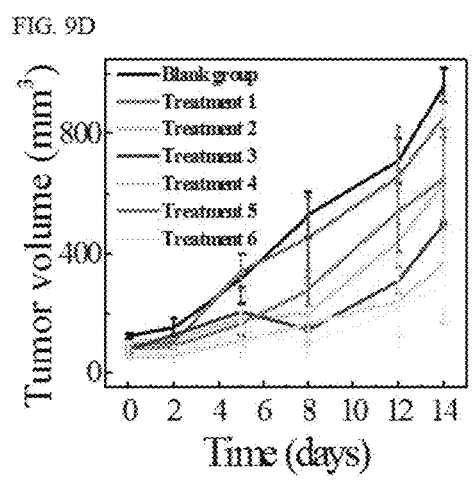

SEQUENCE LISTING

```
<160> NUMBER OF SEQ ID NOS: 5

<210> SEQ ID NO 1
<211> LENGTH: 142
<212> TYPE: DNA
<213> ORGANISM: artificial sequence
<220> FEATURE:
<223> OTHER INFORMATION: ssDNA

<400> SEQUENCE: 1
atagtgagtc gtattaaaaa aaaaccgtta ccatcttgag tgtgaccact ccattgtcct      60
aggccaccaa gatctgaacg gttgaaaaaa agtcacctca cttcgaacag gaagtaaggt     120
ggcctcagac gaaaaaatcc ct                                             142

<210> SEQ ID NO 2
<211> LENGTH: 142
<212> TYPE: DNA
<213> ORGANISM: artificial sequence
<220> FEATURE:
```

-continued

```
<223> OTHER INFORMATION: ssDNA for scrambled shRNA

<400> SEQUENCE: 2
atagtgagtc gtattaaaaa aggacaactg ccatcgccgt cactgatatt tcatgattct      60
actagggatt ccgccacagg acataaaaag ctgaggaaag tccagtgaac gaacataccc     120
tagcgtgacc taaaaaatcc ct                                              142

<210> SEQ ID NO 3
<211> LENGTH: 48
<212> TYPE: DNA
<213> ORGANISM: artificial sequence
<220> FEATURE:
<223> OTHER INFORMATION: CpG

<400> SEQUENCE: 3
aaaatcccta tagtgagtcg tattaaaatc catgacgttc ctgacgtt                   48

<210> SEQ ID NO 4
<211> LENGTH: 22
<212> TYPE: DNA
<213> ORGANISM: artificial sequence
<220> FEATURE:
<223> OTHER INFORMATION: T7 promotor

<400> SEQUENCE: 4
taatacgact cactataggg at                                               22

<210> SEQ ID NO 5
<211> LENGTH: 91
<212> TYPE: DNA
<213> ORGANISM: artificial sequence
<220> FEATURE:
<223> OTHER INFORMATION: F-C-LXLapt-Chol

<400> SEQUENCE: 5
cactccattg tcctaggcga attcagtcgg acagcgaagt agttttcctt ctaacctaag      60
aacccgcggc agtttaatgt agatggacga a                                    91
```

PREPARATION AND USE OF NANOPARTICLE-DOPED RNA HYDROGEL TARGETING TO TRIPLE NEGATIVE BREAST CANCER

RELATED APPLICATION

The present application claims priority to Chinese Application No. 201910648136.6, filed Jul. 18, 2019, and is hereby incorporated by reference in its entirety into the present application.

INCORPORATION BY REFERENCE

The sequence listing provided in the file entitled EFILED-_SEQUENCE_LISTING_txt.txt, which is an ASCII text file that was created on Jul. 18, 2019, and which comprises 2048 bytes, is hereby incorporated by reference in its entirety.

TECHNICAL FIELD

The present invention relates to the technical field of biochemical nanomaterials, and in particular to preparation and use of a nanoparticle-doped RNA hydrogel targeting to a triple negative breast cancer, achieving multiple synergistic and gain treatment of the triple negative breast cancer.

BACKGROUND

The breast cancer is one of the most common cancers in women. A triple negative breast cancer (TNBC) refers to a type of breast cancer that lacks the expression of an estrogen receptor (ER), a progesterone receptor (PR) and a human epidermal growth factor receptor 2 (HER2). Clinical studies have shown that TNBC is the most aggressive type of breast cancer compared to other types of breast cancers, with poor prognosis and being more difficult to control in mortality and a metastasis tendency. Traditional therapies include a hormonal therapy, and a targeted therapy of three receptors, but the treatment effect is barely satisfactory. Therefore, it is urgent and important to develop a TNBC diagnosis and combined therapy more effectively.

The ectopic expression of microRNA-205 can reduce in vitro cell proliferation, inhibit in vivo tumor growth by targeted inhibition of E2F1 and LAMC1, where the E2F1 is a cell cycle regulator, and the LAMC1 an ingredient of extracellular matrix that is involved in cell adhesion, proliferation and migration. microRNA-182 affects cell motility and metastasis of breast cancer cells by precisely inhibiting the expression of a Palladin protein. Studies have shown that, microRNAs are statistically significant in cancer treatment, but the prognosis of an individual microRNA is not ideal.

Manganese dioxide can be decomposed with endogenous hydrogen peroxide or glutathione in a tumor microenvironment to produce oxygen, and the generated manganese ions can be easily discharged from the body, rather than staying in the body to affect the health of the body; and meanwhile, the generated oxygen can be used for enhanced photodynamic therapy. During the performance of the photodynamic therapy, an exogenous laser can promote the DOX to be unloaded from the hydrogel, and thus it can be accumulated in a cell nucleus in a short time, thereby rapidly killing the tumor cells.

The used aptamer is an aptamer selected through screening by the research group of Yang Chaoyong in Xiamen University. The aptamer specifically binds to an MDA-MB-231 cell surface receptor, thereby achieving targeted dosing. An RNA gene nanoprobe, which is constructed as a control group in the subsequent experimental work, also has a certain targeted therapeutic effect.

Cholesterol (Chol), which is hydrophobic, can facilitate the formation of a nanostructure of an RNA transcription copy while also enhancing the structural stability.

There is an urgent need to study an emerging hydrogel and a preparation method thereof, the hydrogel being formed just by self-assembly of RNA molecules and being highly effective in the treatment of the triple negative breast cancer.

SUMMARY

The technical problem to be solved by the present invention is to provide a hydrogel, which is formed just by self-assembly of RNA molecules and has the advantages of high efficiency, low toxicity, good biocompatibility, and the like, as a vector to carry various therapeutic drug targeted into a triple negative breast cancer.

The technical solution of the present invention is as follows.

An RNA hydrogel vector for targeted therapy of a triple negative breast cancer, includes:

(1) an RNA hydrogel formed from a linear DNA transcription template by rolling circle transcription, (2) therapeutic genes microRNA-182 and microRNA-205 on the RNA hydrogel.

Further, the linear DNA transcription template has a nucleotide sequence as shown in SEQ ID No. 1, and is phosphorylated at a 5' terminus.

A method for preparing an RNA hydrogel vector is disclosed, where first a linear DNA transcription template is designed, antisense sequences of microRNA-182 and microRNA-205 are designed in the linear DNA transcription template, and a hydrogel vector of a pure RNA system is formed by rolling circle transcription.

Further, the specific steps are as follows:

(1) subjecting a linear DNA transcription template and a T7 promoter to an annealing treatment at the same concentration;

(2) adding a T4 ligase and a T4 ligase buffer, and maintaining at 19° C. for 13 h to form an RNA transcription template;

(3) adding a T7 polymerase, rNTP, a T7 polymerase buffer and a TM buffer, and maintaining at 37° C. for 5 h to form a multi-copy RNA hydrogel vector.

An RNA hydrogel complex for targeted therapy of a triple negative breast cancer, included:

(1) an RNA hydrogel formed from a linear DNA transcription template by rolling circle transcription, (2) therapeutic genes microRNA-182 and microRNA-205 on the RNA hydrogel.

(3) an aptamer, a CpG fragment and a DOX on the RNA hydrogel; and (4) colloidal $MnO_2$@Ce6 cationic nanoparticles adhered by an electrostatic action.

Further, the linear DNA transcription template has a nucleotide sequence as shown in SEQ ID No.1, and is phosphorylated at a 5' terminus.

Further, the aptamer is an aptamer targeting to a MDA-MB-231 cell, which has a nucleotide sequence as shown in SEQ ID No.5, and is modified with a Fam group at a 5' terminus and modified with cholesterol at a 3' terminus; and the CpG fragment is the nucleotide sequence as shown in SEQ ID No.3, and is modified with a Fam group at a 5' terminus and modified with cholesterol at a 3' terminus.

A method for preparing a RNA hydrogel complex is disclosed, where first a linear DNA transcription template is designed, antisense sequences of microRNA-182 and microRNA-205 are designed in the linear DNA, a hydrogel vector of a pure RNA system is formed by rolling circle transcription, added with a CpG fragment, a aptamer and a DOX, and centrifuged to form an RNA triple helix hydrogel, and then added with colloidal $MnO_2$@Ce6 cationic nanoparticles to obtain a RNA hydrogel complex.

Further, the specific steps are as follows:

(1) subjecting a linear DNA transcription template and a T7 promoter to an annealing treatment at the same concentration;

(2) adding a T4 ligase and a T4 ligase buffer, and maintaining at 19° C. for 13 h to form an RNA transcription template;

(3) adding a T7 polymerase, rNTP, a T7 polymerase buffer and a TM buffer, and maintaining at 37° C. for 5 h to form a multi-copy RNA hydrogel vector; and (4) maintaining the RNA hydrogel vector obtained from step (3), the TM buffer, the CpG fragment and the aptamer at 65° C. for 5 min, gradually reducing the temperature to 25° C., placing in a refrigerator at 4° C. for 2 h, mixing with the DOX at 37° C. for 2 h, and then centrifuging at a high speed to form an RNA triple helix hydrogel; and then being allowed to stand at room temperature for 15 min together with the colloidal $MnO_2$@Ce6 cationic nanoparticles, so as to obtain the RNA hydrogel complex.

Further, the method of an annealing treatment is: heating to 95° C. for 5 min in a TM buffer, followed by cooling to 25° C. at 1° C./min for 30 min. The composition of the TM buffer is: 30 mM $MgCl_2$, 10 mM Tris-HCl, pH=8.0.

Disclosed is the use of the RNA hydrogel carrier or RNA hydrogel complex of the present invention in the preparation of a related medicament for treating a triple negative breast cancer.

The colloidal $MnO_2$@Ce6 in the present invention is synthesized according to a method reported in previous studies, and in brief is obtained by reducing $KMnO_4$ with PAH, then being subjected to ultrasonic treatment with a photosensitizer Ce6 for 4 h, and then centrifuging.

In the present invention, the DOX is adriamycin.

Compared with the prior art, the present invention has the following beneficial effects:

In the present invention, the vector is a pure RNA system formed by rolling circle transcription, where during the process of transcription and replication therapeutic genes microRNA-182 and microRNA-205 are generated, and bind to the aptamer targeting to triple negative breast cancer cells and the CpG fragment having an immunostimulatory effect through a complementary base pairing principle, are designed with cholesterol on the complementary sequence of the aptamer, and centrifuged at a high speed to form the RNA hydrogel. The transcription process generates a large number of GC bonds, which provides a large number of sites for the introduction of DOX. The large number of RNA copy structures generated by rolling circle replication is a polyanionic aggregate. Due to the strong electronegativity of the polyanionic aggregate, electropositive $MnO_2$@Ce6 nanoparticles are introduced, such that the colloid cationic $MnO_2$@Ce6 particles can be stabilized by the polyanionic hydrogel, and thus target into a breast cancer cell for synergistic treatment. The $MnO_2$@Ce6-loaded hydrogel is successfully applied in a drug slow release system, has good biocompatibility, and has broad prospects in the fields of growth inhibition effects on targeted MDA-MB-231 tumor cells, inhibition of cancer metastasis and recurrence, and the like.

BRIEF DESCRIPTION OF THE DRAWINGS

FIGS. 7A, 7B, 7C, 7D, 8A, 8B, 8C and 8D are diagrams of confocal microscopic imaging and flow cytometry analysis;

FIGS. 9A, 9B, 9C and 9D are a cytotoxicity map and mouse tumor size tracking map.

DESCRIPTION OF THE EMBODIMENTS

Figure 1:
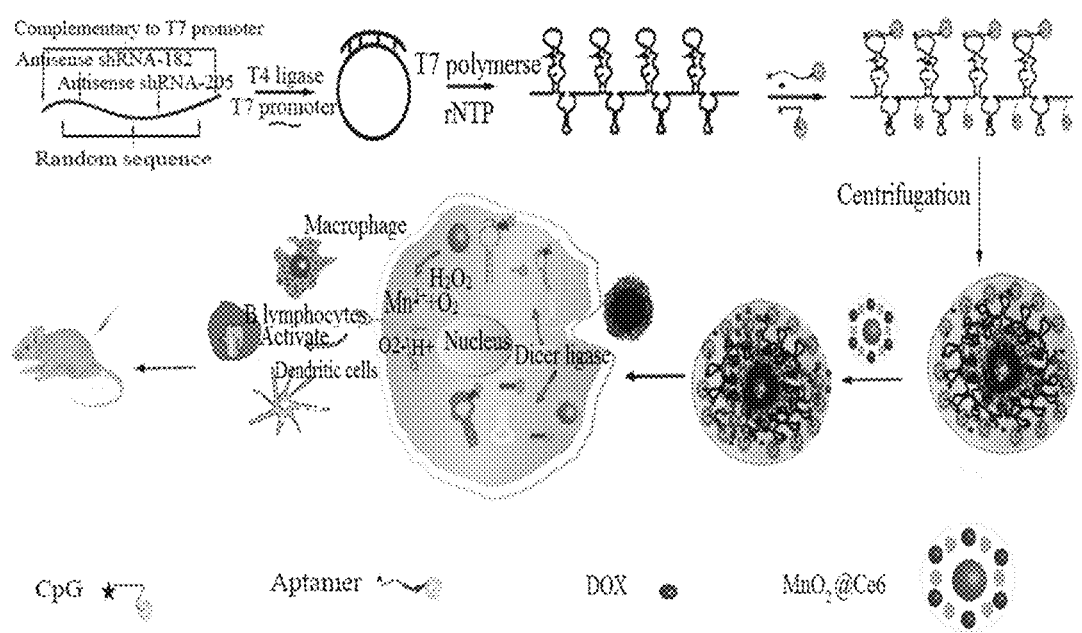
FIG. 1 is a schematic diagram of the diagnosis and treatment of a triple negative breast cancer in vitro and in vivo by Hydrogel/DOX-$MnO_2$@Ce6.

The oligonucleotide sequences used in the present invention are as shown in Table 1.

TABLE 1

| Oligonucleotide sequences as used | |
|---|---|
| ssDNA | 5'-phosphate-ATAGTGAGTCGTATTA AAAAA AAA CCG TTA CCA TCT TGA GTG TGA CCA CTC CAT TGT CCT AGG CCA CCA AGA TCT GAA CGG TTGAAAAAAAG TCA CCT CAC TTC GAA CAG GAA GTA AGG TGG CCT CAG ACGAAAAAATCCCT-3' (SEQ ID NO. 1) |
| ssDNA for scrambled shRNA | 5'-phosphate-ATAGTGAGTCGTATTA AAAAA GGA CAA CTGCCA TCG CCG TCA CTG ATA TTT CAT GAT TCT ACT AGG GAT TCC GCC ACA GGA CATAAAAAGCT GAG GAA AGT CCA GTG AAC GAA CAT ACC CTA GCG TGA CCTAAAAAATCCCT-3' (SEQ ID NO. 2) |
| CpG | 5'-FAM-AAA ATCCC TATAG TGAGT CGTAT TA AAATCC ATG ACG TTC CTG ACG TT---Chol-3' (SEQ ID NO. 3) |
| T7 promotor: | 5'-TAA TAC GAC TCA CTA TAG GGA T-3' (SEQ ID NO.4) |
| F-C-LXLapt-Chol | 5'-FAM-CAC TCC ATT GTC CTA GGCGAA TTC AGT CGG ACA GCG AAG TAG TTT TCC TTC TAA CCT AAG AAC CCG CGG CAG TTT AAT GTA GAT GGA CGA A-Chol-3' (SEQ ID NO. 5) |

Example 1

An RNA hydrogel vector for targeted therapy of a triple negative breast cancer, includes:

(1) an RNA hydrogel formed from a linear DNA transcription template (the ssDNA in table 1) by rolling circle transcription; and (2) therapeutic genes microRNA-182 and microRNA-205 on the RNA hydrogel.

First, a single-stranded DNA template (ssDNA in Table 1) of which both termini could be complementary paired with primers for a T7 promoter (T7promotor in Table 1) was designed. The single-stranded DNA contained the complementary sequence of each shRNA as involved by us (antisense sequences of microRNA-182 and microRNA-205). A large amount of shRNA-182 and shRNA-205 copies was transcribed by rolling circle transcription at a low cost for using as gene therapy fragments and meanwhile also using as a vector for DOX and the immune gene CpG, such that a multi-functional intelligent nano-agent which integrated gene therapy, chemical agent treatment and combined immunotherapy was obtained, achieving integrated research on the diagnosis and treatment of the triple-negative breast cancer.

The specific steps were as follows:

(1) subjecting a linear DNA transcription template (ssDNA in Table 1) and a T7 promoter(T7promotor in Table 1) to an annealing treatment at the same concentration;

(2) adding a T4 ligase and a T4 ligase buffer, and maintaining at 19° C. for 13 h to form an RNA transcription template; and (3) adding a T7 polymerase, rNTP, a T7 polymerase buffer and a TM buffer, and maintaining at 37° C. for 5 h to form a multi-copy RNA hydrogel vector.

Example 2

An RNA hydrogel complex for targeted therapy of a triple negative breast cancer, included:

(1) an RNA hydrogel formed from a linear DNA transcription template (the ssDNA in table 1) by rolling circle transcription;

(2) therapeutic genes microRNA-182 and microRNA-205 on the RNA hydrogel.

(3) the aptamer (FC-LXLapt-Chol in Table 1), CpG fragment (CpG in Table 1) and DOX (adriamycin) on the RNA hydrogel; and (4) colloidal $MnO_2$@Ce6 cationic nanoparticles adhered by an electrostatic action.

A method for preparing a RNA hydrogel complex is disclosed, where first a linear DNA transcription template is designed, antisense sequences of microRNA-182 and microRNA-205 are designed in the linear DNA, a hydrogel vector of a pure RNA system is formed by rolling circle transcription, added with a CpG fragment, a aptamer and a DOX, and centrifuged to form an RNA triple helix hydrogel, and then added with colloidal $MnO_2$@Ce6 cationic nanoparticles to obtain a RNA hydrogel complex.

The specific steps were as follows:

(1) subjecting a linear DNA transcription template (ssDNA in Table 1) and a T7 promoter(T7promotor in Table 1) to an annealing treatment at the same concentration;

(2) adding a T4 ligase and a T4 ligase buffer, and maintaining at 19° C. for 13 h to form an RNA transcription template;

(3) adding a T7 polymerase, rNTP, a T7 polymerase buffer and a TM buffer, and maintaining at 37° C. for 5 h to form a multi-copy RNA hydrogel vector; and (4) maintaining the RNA hydrogel vector obtained from step (3), the TM buffer, the CpG fragment (CpG in table 1) and the aptamer (F-C-LXLapt-Chol in table 1) at 65° C. for 5 min, gradually reducing the temperature to 25° C., placing in a refrigerator at 4° C. for 2 h, mixing with the DOX at 37° C. for 2 h, then mixing the aforementioned reaction product with double distilled water (DI water) at a ratio of 1: centrifuging at a speed of 8000 rpm twice, each for 5 min, finally redistributing in 50 μL of deionized water to form DNA nanogel, and storing in a refrigerator at 4° C. for later use. After a series of reactions, a micro-sponge-like nanosphere was finally formed. The hydrogel is allowed to stand at room temperature for 15 min together with the synthesized colloidal $MnO_2$@Ce6 nanoparticles to obtain an RNA hydrogel complex.

The method of an annealing treatment was: heating to 95° C. for 5 min in a TM buffer, followed by cooling to 25° C. at 1° C./min for 30 min. The composition of the TM buffer is: 30 mM $MgCl_2$, 10 mM Tris-HCl, pH=8.0.

The colloidal $MnO_2$@Ce6 in the present invention is synthesized according to a method reported in previous studies, and in brief is obtained by reducing $KMnO_4$ with PAH, then being subjected to ultrasonic treatment with a photosensitizer Ce6 for 4 h, and then centrifuging.

Figure 2:
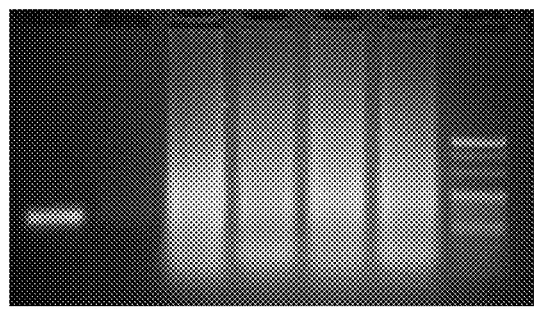
FIG. 2 is a characterization of different stages of a macromolecular hydrogel by 2% agarose gel electrophoresis.
Figure 3:
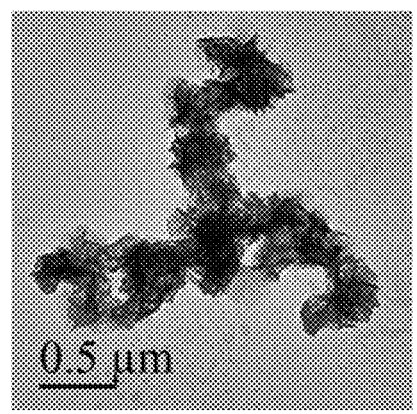
FIG. 3 is a TEM (transmission electron microscope) characterization map of a hydrogel.
Figure 4:
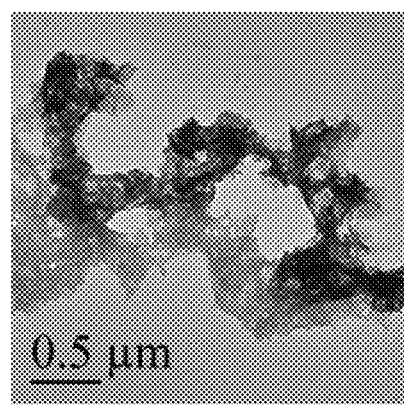
FIG. 4 is an electron microscope characterization map of Hydrogel/DOX-$MnO_2$@Ce6.
Figure 5:
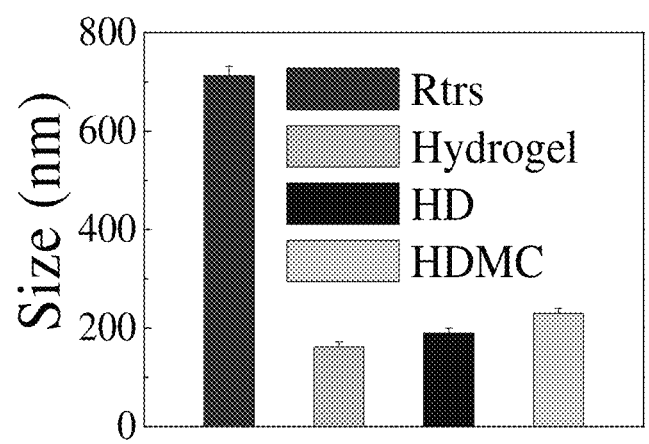
FIG. 5 is a diagram showing particle sizes of the hydrogel at four different stages.
Figure 6:
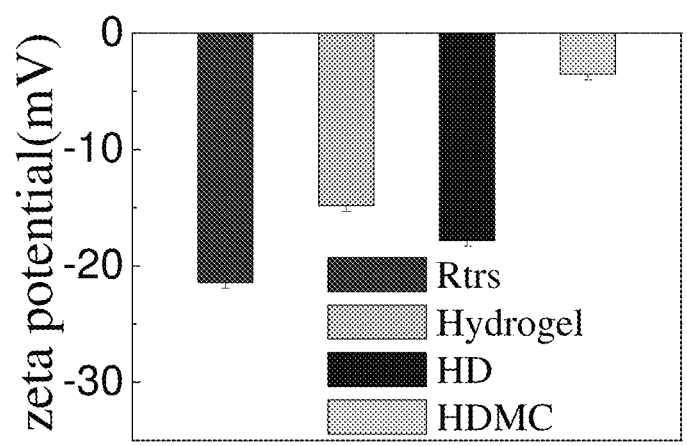
FIG. 6 is a diagram showing the zeta potential of the hydrogel at four different stages.

Experimental Example (1) To determine the formation of hydrogel at each stage, the hydrogel product of each stage was subjected to characterization by transmission electron microscopy (the DOX-loaded RNA hydrogel vector as shown in FIG. 3, and the $MnO_2$@Ce6-loaded RNA hydrogel vector as shown in FIG. 4), agarose gel electrophoresis (as shown in FIG. 2, the first band was a linear DNA, the second band was a circular DNA transcription template, the third band was a rolling circle product, the fourth band was a band for modified CPG, the fifth band was a band for a modified aptamer, the sixth band was a band for the modified CPG and the aptamer, and the seventh band was a marker at 500 bp) and a particle size analyzer (FIG. 5 showed a particle size, and FIG. 6 showed a zeta potential, where Rtrs represented a transcriptional copy, Hydrogel represented a hydrogel that was modified with the aptamer and the CpG fragment, HD represented a DOX-loaded Hydrogel, and HDMC represented the binding of the DOX-loaded Hydroge with $MnO_2$@Ce6).

(2) For the characterization of targeted uptake of the RNA triple helix nanohydrogel by a cell, the specific operation process was as follows:

The MDA-MB-231 cells were placed and incubated in a 35 mm glass button petri dish under the condition of 37° C. for 24 h until the cell density reached about 80%, then added with the hydrogel and co-incubated for 2 h, and added with a DAPI nuclear staining reagent to mark the location of the cell nucleus, The culture medium was removed with PBS, and the cells were resuspended in 1 mL PBS, photographed by confocal microscopy for the position of uptaking the RNA triple helix hydrogel by a cell, as shown in the panel a of FIG. 7. After the end of the confocal microscopy, the cells were collected into a 1.5 mL centrifuge tube, and were subjected to flow cytometry determination to obtain a flow cytometry diagram as shown in the panel b of FIG. 7. The cells were added with the DOX-loaded hydrogel and co-incubated for 2 h, and added with the DAPI nuclear staining reagent to mark the location of the cell nucleus. The culture medium was removed with PBS, and the cells were resuspended in 1 mL PBS, photographed by confocal microscopy to obtain the distribution of the DOX-loaded hydrogel as uptaken after the cells were irradiated by a laser light at 650 nm, as shown in the panel c of FIG. 7. Therefore, it could be seen that, the enrichment of DOX at the cell nucleus could be accelerated under irradiation of laser light. The cells were added with and then co-incubated with the DOX-loaded hydroge and $MnO_2$@Ce6(HDMC) for 2 h. The culture medium was removed with PBS, and the cells were resuspended in 1 mL PBS, photographed by confocal microscopy to obtain the cell uptake conditions as shown in the panel a of FIG. 8, and photographed by confocal microscopy to obtain the distribution of HDMC as uptaken after the cells were irradiated by a laser light at 650 nm, as shown in the panel b of FIG. 8. Therefore, it could be seen that, Ce6 entered the cell successfully, and emitted a strong fluorescence signal as excited by the laser light at 650 nm, and meanwhile the intracellular fluorescent signals were collected by flow cytometry to obtain panels c and d of FIG. 8.

(3) Cytotoxicity Experiment with CCK-8 Kit:

First 100 μL of a cell suspension was formulated in a 96-well plate, and the culture plate was pre-incubated in an incubator at 37° C. under 5% $CO_2$ for 24 h. the culture plate was added with 10 μL of different kinds of drugs to be tested, and incubated in an incubator for a certain period of time. The original culture medium was discarded and replaced with 100 μL of a fresh culture medium, and then each well was added with 10 μL of a CCK-8 solution (it should be noted that no bubble was allowed to be formed in the well, otherwise it would affect the reading of the OD value), continued to incubate in the incubator for an appropriate period of time, and determined with a microplate reader for the absorbance at 450 nm. A well for which the cell suspension was only added with CCK-8 and not added with the substance to be tested, was selected as a control well, and the culture medium containing no cells was selected to be added to CCK-8 as a blank group, and the experiment was performed. The final cell viability %=[A (dosing)–A (blank)]/[A (dosing of 0)–A (blank)]×100%.

The results were as shown in panels a and b of FIG. 9. Under the equal conditions, the rolling circle transcription copies in both the experimental group and the control group had almost no effect on the cell viability, and with the gradual increase of the therapeutic agent, the cell viability was also decreased gradually.

4. In Vivo Detection Experiment

First a 4T1 cell subcutaneous tumor-bearing mouse model was established, where one group was used as a blank group that was injected with the buffer solution (the TM buffer) used in the experiment; one group was set as a control group that was injected intratumorally with a series of hydrogel drugs of any gene sequence; and one group was set as the experimental group that was injected intratumorally with a series of hydrogel drugs of therapeutic gene sequences. The injection dose of each group was 30 μL per injection, and the injection frequency was consistent among the groups. After the injection operation, continuous tracking and observation were conducted, to track and record the tumor volumes of mice (tumor volume changes of mice in the blank group and the control group as shown in panel c of FIG. 9C, and tumor volume changes of mice in the blank group and the experimental group as shown in panel d of FIG. 9D). After the end of the experiment, the mice were sacrificed by a carbon dioxide asphyxiation method, and the tumors and visceral organs of the mice of each group were peeled off.

Figure 10:
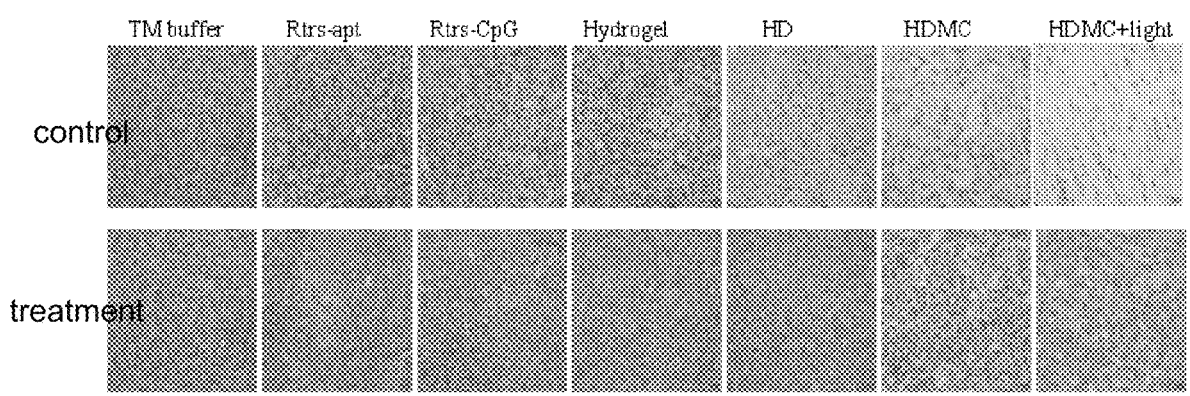
FIG. 10 shows the H&E staining analysis of mouse tumors.

FIG. 10 was a graph showing the analysis of the H&E staining data of tumors in murine breast cancer (4T1) tumor-bearing mice after they were administrated with the TM buffer, a series of hydrogels of any gene sequence, and a series of hydrogels of therapeutic gene sequences. It could be seen from the figure that, the tumor cell nucleus of the control group was richer than that of the treatment group, and thus it could be seen that the additive treatment effect was better, and the morphology of the tumor cell was severely damaged.

In view of the above, the hydrogel complex vector as designed in the research for the targeted treatment of the triple negative breast cancer achieved a multiple synergistic and gain treatment method, realizing targeted triple gene therapy for tumor cells. The effects of the hydrogel in this experiment were mainly presented in the following several aspects: (1) linking a aptamer that is targeted to MDA-MB-231; (2) realizing gene therapy for the triple negative breast cancer by microRNA-182 and microRNA-205 through a gene replacement method; and (3) acting as a vector to targeted bring the therapeutic gene, the chemical agent DOX, and $MnO_2$@Ce6 for treating and improving the tumor microenvironment into tumor cells for synergistic gain therapy. By adopting laser confocal imaging and flow cytometry detection, the uptaken amount of the hydrogel by triple negative breast cancer cells in vitro was analyzed, and cytotoxicity verification was conducted using CCK8. A wild mouse model was established. By tracking the body weights of the mice, a good therapeutic effect was shown in tumor size and later pathological analysis.

What is claimed is:

1. An RNA hydrogel vector for targeted therapy of a triple negative breast cancer, comprising:
    an RNA hydrogel formed from a linear DNA transcription template by rolling circle transcription; and
    therapeutic genes microRNA-182 and microRNA-205 on the RNA hydrogel,
    wherein the linear DNA transcription template has a nucleotide sequence as shown in SEQ ID No.1, and is phosphorylated at a 5' terminus.

2. A method for preparing the RNA hydrogel vector according to claim 1, wherein first a linear DNA transcription template is designed, antisense sequences of microRNA-182 and microRNA-205 are designed in the linear DNA transcription template, and a hydrogel vector of a pure RNA system is formed by rolling circle transcription.

3. A method for preparing the RNA hydrogel vector according to claim 1, comprising the following specific steps:
    (1) subjecting a linear DNA transcription template and a T7 promoter to an annealing treatment at the same concentration;
    (2) adding a T4 ligase and a T4 ligase buffer, and maintaining at 19° C. for 13 h to form an RNA transcription template; and
    (3) adding a T7 polymerase, rNTP, a T7 polymerase buffer and a TM buffer, and maintaining at 37° C. for 5 h to form a multi-copy RNA hydrogel vector.

4. An RNA hydrogel complex for targeted therapy of a triple negative breast cancer, comprising:
    an RNA hydrogel formed from a linear DNA transcription template by rolling circle transcription;
    therapeutic genes microRNA-182 and microRNA-205 on the RNA hydrogel;
    an aptamer, a CpG fragment and a DOX on the RNA hydrogel; and
    colloidal $MnO_2$@Ce6 cationic nanoparticles adhered by an electrostatic action,
    wherein the linear DNA transcription template has a nucleotide sequence as shown in SEQ ID No.1, and is phosphorylated at a 5' terminus.

5. The RNA hydrogel complex according to claim 4, wherein the aptamer is an aptamer targeting to a MDA-MB-231 cell, which has a nucleotide sequence as shown in SEQ ID No.5, and is modified with a Fam group at a 5' terminus and modified with cholesterol at a 3' terminus; and the CpG fragment is the nucleotide sequence as shown in SEQ ID No.3, and is modified with a Fam group at a 5' terminus and modified with cholesterol at a 3' terminus.

6. A method for preparing the RNA hydrogel complex according to claim 4, wherein first a linear DNA transcription template is designed, antisense sequences of microRNA-182 and microRNA-205 are designed in the linear DNA, a hydrogel vector of a pure RNA system is formed by rolling circle transcription, added with a CpG fragment, a aptamer and a DOX, and centrifuged to form an RNA triple helix hydrogel, and then added with colloidal MnO$_2$@Ce6 cationic nanoparticles to obtain a magnetic RNA hydrogel complex.

7. The method for preparing the RNA hydrogel complex according to claim 6, comprising the following specific steps:
   (1) subjecting a linear DNA transcription template and a T7 promoter to an annealing treatment at the same concentration;
   (2) adding a T4 ligase and a T4 ligase buffer, and maintaining at 19° C. for 13 h to form a RNA transcription template;
   (3) adding a T7 polymerase, rNTP, a T7 polymerase buffer and a TM buffer, and maintaining at 37° C. for 5 h to form a multi-copy RNA hydrogel vector; and
   (4) maintaining the RNA hydrogel vector obtained from step (3), the TM buffer, the CpG fragment and the aptamer at 65° C. for 5 min, gradually reducing the temperature to 25° C., placing in a refrigerator at 4° C. for 2 h, mixing with the DOX at 37° C. for 2 h, and then centrifuging at a high speed to form an RNA triple helix hydrogel; and then being allowed to stand at room temperature for 15 min together with the colloidal MnO$_2$@Ce6 cationic nanoparticles, so as to obtain the RNA hydrogel complex.

8. A method for preparing the RNA hydrogel complex according to claim 6, wherein first a linear DNA transcription template is designed, antisense sequences of microRNA-182 and microRNA-205 are designed in the linear DNA, a hydrogel vector of a pure RNA system is formed by rolling circle transcription, added with a CpG fragment, a aptamer and a DOX, and centrifuged to form an RNA triple helix hydrogel, and then added with colloidal MnO$_2$@Ce6 cationic nanoparticles to obtain a magnetic RNA hydrogel complex.

9. A method for preparing the RNA hydrogel complex according to claim 7, wherein first a linear DNA transcription template is designed, antisense sequences of microRNA-182 and microRNA-205 are designed in the linear DNA, a hydrogel vector of a pure RNA system is formed by rolling circle transcription, added with a CpG fragment, a aptamer and a DOX, and centrifuged to form an RNA triple helix hydrogel, and then added with colloidal MnO$_2$@Ce6 cationic nanoparticles to obtain a magnetic RNA hydrogel complex.

* * * * *